United States Patent [19]

Savello et al.

[11] Patent Number: 5,368,869
[45] Date of Patent: Nov. 29, 1994

[54] COMPOSITIONS AND METHODS FOR MANUFACTURING A SKIM OR LOWFAT MILK PRODUCT WITH INCREASED CREAMINESS, COLOR, MOUTHFEEL, AND TASTE SENSATIONS SIMILAR TO MILK WITH A HIGHER FAT CONTENT

[75] Inventors: Paul A. Savello, Hyde Park, Utah; Hector A. Solorio, Parma, Id.

[73] Assignee: Utah State University Foundation, Logan, Utah

[21] Appl. No.: 28,279

[22] Filed: Mar. 9, 1993

[51] Int. Cl.⁵ .............................................. A23C 9/12
[52] U.S. Cl. ..................................... 426/42; 426/580; 426/583; 426/800
[58] Field of Search ................. 426/42, 580, 800, 583, 426/34

[56] References Cited

U.S. PATENT DOCUMENTS

| | | | |
|---|---|---|---|
| 4,347,258 | 8/1982 | Merkenich et al. | 426/334 |
| 4,413,017 | 11/1983 | Loader | 426/616 |
| 4,513,017 | 4/1985 | Moran et al. | 426/603 |
| 4,908,223 | 3/1990 | Murtaugh et al. | 426/565 |

OTHER PUBLICATIONS

The Condensed Chemical Dictionary, 10th Ed., Revised by G. Hawley, VNR Co., New York, 1981, p. 257.

*Primary Examiner*—Donald E. Czaja
*Assistant Examiner*—Curtis E. Sherrer
*Attorney, Agent, or Firm*—Workman, Nydegger & Jensen

[57] ABSTRACT

Novel compositions and methods are disclosed for lowfat and skim milk products which have an increased creamy mouthfeel, whiter color, and taste sensations similar to milk with a high fat content. The textured milk products involves skim milk and lowfat milk being treated with a milk coagulant to partially coagulate and aggregate proteins in the milk. The enzyme-treated milks are heat-processed to denature the coagulating enzyme. The finished milk products are then cooled and stored at an appropriate refrigeration temperature.

81 Claims, 8 Drawing Sheets

COMPOSITIONS AND METHODS FOR MANUFACTURING A SKIM OR LOWFAT MILK PRODUCT WITH INCREASED CREAMINESS, COLOR, MOUTHFEEL, AND TASTE SENSATIONS SIMILAR TO MILK WITH A HIGHER FAT CONTENT

BACKGROUND

1. The Field of the Invention

The present invention relates to compositions and methods of manufacture of an improved skim or lowfat milk product. In particular, the preferred embodiment of the invention relates to compositions and methods of manufacture of a textured type of skim or lowfat milk which is produced by treating skim or lowfat milk with a milk coagulant to partially coagulate and aggregate proteins in the milk. The enzyme-treated milk is then heat processed in order to denature the coagulating enzyme. The finished milk product is then cooled to and stored at an appropriate refrigeration temperature. The final product not only has an increased creamy mouthfeel, but also is characterized by a white color and taste sensations similar to milk with a higher fat content.

2. The Background Art

Milk is a unique product obtained by the secretion of the mammary glands of mammals and is intended for nutrition of the young. Milk provides those nutrients on which many living organisms depend for continued health and growth. The consumption of milk in the United States has become an important aspect of human nutrition. Moreover, because most individuals like the taste of milk, its presence in the marketplace is demanded.

Unfortunately, milk products are generally high in fat content. Americans are becoming increasingly selective about the milk products they consume because of the health problem in later life often associated with the consumption of large quantities of fat. The presence of large amounts of fats in the human body can lead to the deposit of the fats in the arteries. Arterial fat deposits can restrict the circulation of blood which can cause strokes and heart attacks.

At the same time that the public has requested healthier alternatives to presently available milk products, the public has been unwilling to give up flavor or quality in taste of milk products having a high fat content. Generally, even if one milk product is healthier than another milk product, many individuals will eventually return to the milk product which is of a greater quality in terms of taste and flavor. If one type of milk product contains less fat than another milk product, while maintaining acceptable taste, consumers will generally prefer the lower fat-containing product. Indeed, milk products which provide healthy alternatives to the public are eagerly being sought.

Traditionally, the processing of milk results in a change in the composition of the milk. One of the most important processing steps is heating of the milk in order to control the presence of microorganisms. Generally, as the temperature of the milk is increased, microorganisms present in the milk will become deactivated and heat killed.

Heat treatment may be applied to impart other desirable properties. In some products, changes in flavor, color, or viscosity caused by heating may be desired. Heating prior to sterilization may increase the stability of milk proteins to coagulation by subsequent high heat treatments.

The change in flavor from heat treatment of milk proceeds to a "cooked" flavor as the milk temperature increases. This is due to free sulfhydryl groups formed at temperatures above 60° C. The milk then changes to a sterilized milk flavor as the temperature of the milk increases. This is due to the formation of lactones and methylketones from fats.

Still another important processing step is the separation of the milk to yield skim milk and cream. Skim milk has a very low fat content, less than about 0.05%, and this is the milk most health-conscious individuals consume. Nevertheless, skim milk is appropriately berated because of its weak taste and watery mouthfeel. By mixing skim milk and cream, milk may be standardized to a desired fat content to produce the milk products commonly known to most consumers as "1%," "2%," and "whole milk."

The separation of milk to yield skim milk, and even lowfat milk such as 1%, and cream results in the loss of most of the texture or viscosity experienced by the consumption of whole milk. Individuals have submitted that skim milk has a "watery" mouthfeel (i.e., no consistency) due to the absence of fat in the milk (milkfat) in the fluid. Also, the weak flavor and watery color of skim milk is unappealing both to one's taste buds and aesthetic appreciation. Therefore, conventionally prepared and processed skim milk is considered undesirable to the consumer in taste and flavor. Many consumers find the lowfat, 1% or 2% milks also to be unappealing.

Some individuals have attempted to provide a nonfat milk product without the watery texture and taste due to the absence of milkfat in the fluid. Such attempts have involved the addition of nonfat solids into the milk product to provide for some type of texture. The addition of nonfat solids, however, has not met with widespread consumer approval.

Nonfat dry milk powder has been added to fluid skim milk in order to increase the total milk solids of the product. In essence, the nonfat milk solids added in a powder form are similar to the milk solids found in the fluid skim milk. The relative percentages of the constituents of nonfat dry milk powder are in the same relative percentage range as the same constituents in fluid milk.

By adding nonfat dry milk powder to fluid skim milk total protein content, total lactose content, total ash (mineral) content, and total micronutrient content, (e.g., vitamins) all increase to produce a skim milk product with increased total milk solids but with the same relative percentages of each milk constituent (based on dry matter). This process does not lead to consumers being able to perceive an enhanced creaminess or improved mouthfeel sensations because all the milk constituents are in their native (unaltered) state, which does not affect mouthfeel or taste sensations on the tongue.

Other attempts have involved the introduction of fat substitutes into the dairy products. The addition of such fat substitutes gives the impression that fat has been added to the milk product. One commercialized fat substitute product known in the art, produced by such a process, is commonly referred to as SIMPLESSE ®, manufactured by The NutraSweet Corporation. The fat substitute SIMPLESSE ® involves the microparticularization of whey or egg proteins. These proteins are heated, stressed, and restructured, resulting in protein structures that are globularized.

Although a food product produced according to the foregoing process provides a food product which does fool the tongue of consumers without the presence of fat, the process is not without its disadvantages. In particular, the converted proteins presented by the process can only be placed in cold food or dairy products such as ice cream. If placed in heated products, the converted proteins revert to an altered state and do not provide the texture strived for in the milk product.

The restrictive nature of these temperature-sensitive products is immediately apparent. Although cold milk products such as ice cream are popular, the use of milk as an ingredient in cooked foods is considerable. A milk product which reverts to an untextured and tasteless composition when commonly placed in a heated condition is disadvantageous.

Further disadvantages of food products prepared by introduction of fat substitutes include the significantly increased price to the finished food product, the possible need for warning statements to prevent warming of the food product, and the fact that fat substitutes are food additives that require FDA approval and specific labeling requirements. Additionally, the fat substitutes contain caloric value (protein-based fat substitutes contain 4 calories per gram—as does normal protein in foods) which increases the total calories of the finished food product.

In light of the foregoing, it is clear that all of the problems present in the lowfat and particularly skim milk area have not been solved. A market is available for a textured skim milk or lowfat milk which solves these additional problems not remedied by currently known skim or lowfat milks. A need, therefore, exists in the art for compositions of and methods for making a skim or lowfat milk product which is textured so that individuals will believe they are drinking milk with a fat content greater than normal skim or lowfat milks.

A need also exists in the art for compositions of and methods for making a skim or lowfat milk product which fools the tongue of an individual without adding unwanted fats or fat substitutes to the milk product.

Additionally, a need exists in the art for compositions of and methods for making a skim or lowfat milk product having greater consumer acceptability because of the increased creaminess, color, mouthfeel and taste sensations similar to a milk with a higher fat content.

Further, a need exists in the art for compositions of and methods for making a skim or lowfat milk product which is not temperature sensitive so that it can be used as an ingredient in cooking.

Still further, a need exists in the art for compositions of and methods for making a skim or lowfat milk product wherein individuals receive the health benefits from the consumption of milk without a sacrifice due to the presence of fats.

A need also exists in the art for compositions of and methods for making a skim or lowfat milk product having a color and appearance similar to milks with higher fat content.

A further need exists in the art for compositions of and methods for making a skim or lowfat milk product wherein the caloric value is not increased and taste is not diminished.

BRIEF SUMMARY AND OBJECTS OF THE INVENTION

The present invention seeks to resolve problems incident to the consumption of skim and lowfat milk. More specifically, the compositions and methods of this invention constitute an important advance in the milk processing art by providing a textured type of milk product having a perceived increased viscosity which is produced by treating skim or lowfat milk with an enzyme to partially coagulate and aggregate proteins already in the milk. The treated milk is then heat-processed to pasteurize or ultra-pasteurize the product to denature the coagulating enzyme. The finished milk product is then cooled to and stored at an appropriate refrigeration temperature.

The "textured skim milk" invention prepared by the foregoing treatment offers the health-conscious consumer the advantage of its being a nonfat milk product with considerably creamier texture and taste comparable to a milk product with significantly greater amounts of milkfat present.

One object of the present invention is to provide compositions of and methods for making a skim or lowfat milk product which is textured so that individuals will believe they are drinking milk with a fat content greater than normal skim or lowfat milk, Also, it is an object of the present invention to provide compositions of and methods for making a skim or lowfat milk product which fools the tongue of an individual without providing unwanted fats.

Additionally, it is an object of the present invention to provide compositions of and methods for making a skim or lowfat milk product having greater consumer acceptability than normal skim or lowfat milk, due to the increased creaminess, mouthfeel and color.

Still another object of the present invention is to provide compositions of and methods for making a skim or lowfat milk product which is not temperature sensitive and so can be used in cooking.

A further object of the present invention is to provide composition and methods for making a skim or lowfat milk product wherein individuals receive the health benefits from the consumption of milk without a sacrifice due to the presence of fats.

Yet another object of the present invention is to provide compositions of and methods for making a skim or lowfat milk product which has the color and appearance of a milk having a higher fat content.

Another object of the present invention is to provide compositions of and methods for making a skim or lowfat milk product which does not have increased caloric value and which does not decrease flavor.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, is a milk product having substantially the same fat content as skim milk. Because the milk product has substantially the same fat content of skim milk, it can be understood that the fat content of the milk product is quite low. The milk product includes not only pure milk, but also products which comprise the milk of the present invention.

The milk product provides a texture and a sensory experience that is unmistakenly similar to 2% milk or in some cases, whole milk. This texture and sensory experience circumvent the watery taste and texture defects commonly experienced by consumers when drinking skim milk. The texture and sensory experience are present without regard to the temperature of milk product.

The textured milk product of the present invention is produced by the methods disclosed herein. Preferably, the methods for manufacturing the textured milk product comprises treating cold skim or lowfat milk with a coagulating enzyme to partially coagulate and aggregate casein micelles in the milk. It is preferred that a rennet be used as the coagulating enzyme and many types of rennet are available for this use. For example, rennet can be obtained from calves, microorganisms, and plants. The preferred type of rennet is chymosin.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
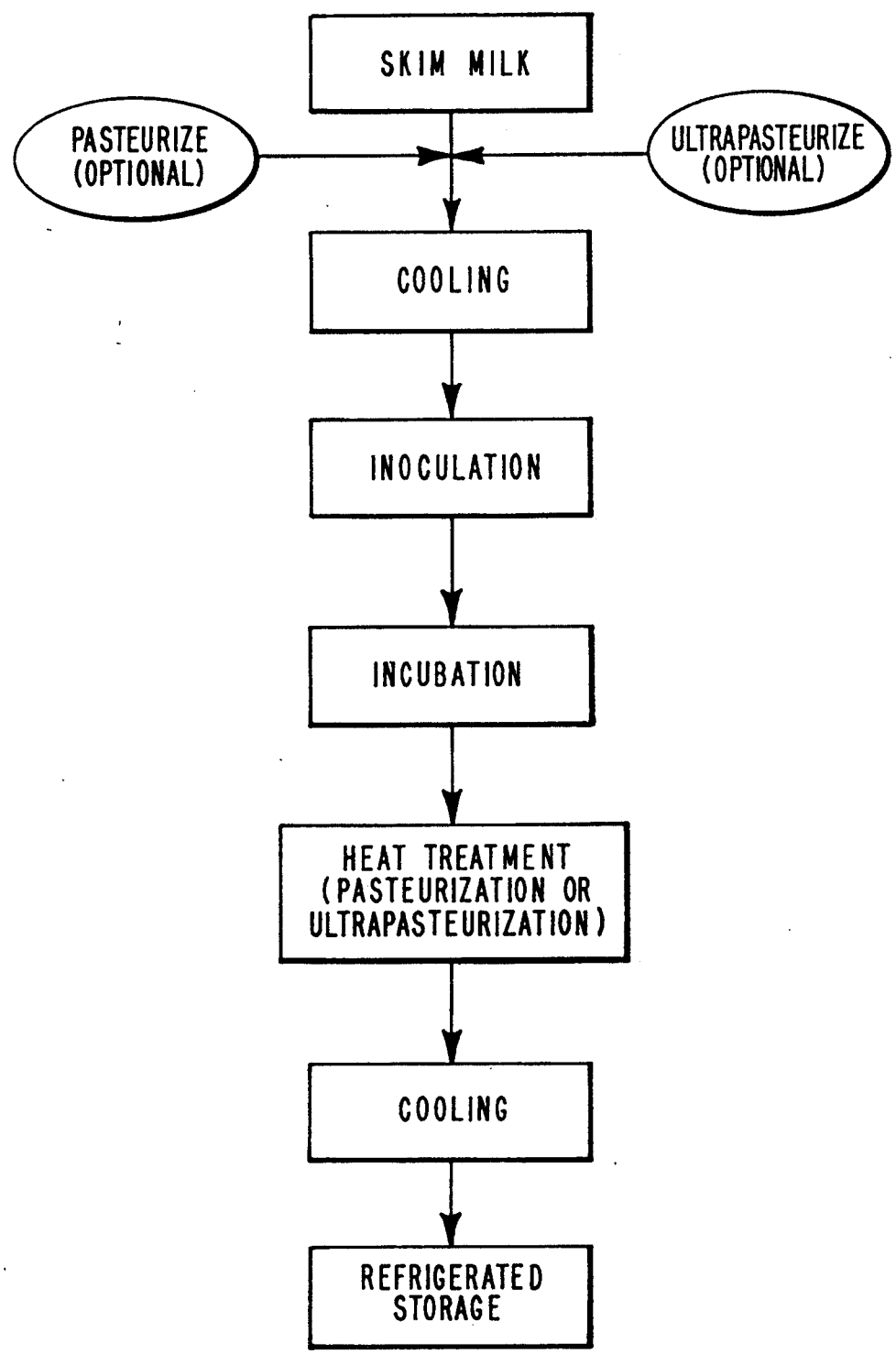
FIG. 1 is a flow chart indicating processing steps which comprise the methods of manufacturing the textured skim or lowfat milk product.

The present invention is directed to novel compositions of and methods for making a more textured and tasteful skim or lowfat milk product. The skim or lowfat milk product of the present invention avoids the watery mouthfeel of known skim or lowfat milks caused by the absence of, or smaller amount of milkfat in the fluid. The skim or lowfat milk product provides flavor and taste sensations that are accepted by consumers. The present invention, where necessary, can be best understood by reference to the drawings, wherein like parts are designated with like numerals throughout.

Although the present invention is best understood by reference to a more textured skim milk beverage product, it should be understood that the present invention is not so limited. Instead, a wide variety of milk products such as the different types of milks, and milk products which comprise milk such as cheeses, puddings, ice cream, and the like are intended to be covered by the present invention. What is important is applying the principles of the present invention to a milk product to provide a textured quality of increased creaminess and mouthfeel similar to milk products having higher amounts of fat. For example, the methods of the present invention can be used for 1% and 2% milks as well as for skim milks. It can be appreciated, however, that the greatest difference will be observed with the milks with lower or no fats.

The understanding of the structure of milk is provided by the following sections A and B. It is believed that the principles and unique features of the present invention can be better understood and discussed with a working knowledge of the materials which comprise the present invention.

A. The Components of Milk

Milk, containing protein, fat, lactose, vitamins, and minerals, together with natural enzymes and those derived from microorganisms within the milk, can be regarded as a relatively complete food. It has a high nutritional value, and it is also an excellent medium for microbial growth.

Lactose is the distinctive sugar of milk. Other carbohydrates are present only in traces. Lactose is a reducing disaccharide composed of glucose and galactose, and is also the principal carbon source for most of the microorganisms that grow in milk. Lactose gives milk a slightly sweet taste.

Milkfat consists of numerous different lipids. More than 98% of milkfat is made up of triglycerides. Cholesterol, diglycerides, free fatty acids, phospholipids, and cerebrosides are also present. The component of fatty acids of milk lipids exhibit a remarkably wide range of 4–20 carbon atoms and 0–4 double bonds.

Milkfat present in milk provides a better mouthfeel and taste because the fat is in a globular form and is sufficiently "slick." This gives the sensation of creaminess, thicker body, or increased mouthfeel. When fat is removed from milk, the milk solids that remain (proteins, lactose, ash, micronutrients) do not have the globular form nor provide a "slick" surface to tell the tongue that the product is richer and creamier.

The minerals in milk are mainly inorganic salts. Some inorganic matter is bound covalently, such as phosphate groups in proteins. When milk is ashed to determine "salt content," ash does not truly represent milk salts because organic salts are destroyed by ashing and some nonsalt components (e.g., sulfur from amino acids) contribute to the ash. Milk contains numerous other elements in trace quantities. For example, salts of organic acids, such as citrate, occur in fresh milk.

Milk also contains several kinds of milk proteins, often classified as caseins, which are a group of phosphate-containing, milk-specific proteins that precipitate upon acidification to pH 4.6 and are necessary for the coagulation and aggregation featured by the present invention. Caseins represent about 80% of the total milk proteins. Sometimes "protein content" is calculated merely by multiplying total nitrogen by a constant factor. However, it should be remembered that about 5% of the nitrogen of milk is present in the form of small molecules, i.e., nonprotein nitrogen.

It is difficult to define caseins in a way that both includes all proteins belonging to the class and excludes all others. Nevertheless, their common property of low solubility at pH 4.6 (at least for bovine milk) serves as a basis for a rather convenient operational definition. At this pH, all of the caseins, except some of the proteolytic derivatives, precipitate.

Compositionally, the hallmark of the caseins is ester-bound phosphate. All of the casein polypeptide chains have at least one such group per molecule.

One of the most common types of casein, and important to the present invention, is the k-casein molecule. About one-third of the k-casein molecules are carbohydrate-free and contain only one phosphate group. It is believed that k-casein, as isolated from milk, consists of a mixture of polymers held together by intermolecular disulfide bonds.

k-Casein is rapidly hydrolyzed by the enzyme chymosin, and by other proteases, yielding an N-terminal fragment called para-k-casein, which contains two cysteine residues, and a C-terminal fragment of 64 residues called the macropeptide. The macropeptide contains all of the carbohydrate and phosphate groups, as well as any genetic substitutions. It should be noted that this hydrolysis reaction, as will be discussed in greater detail at a later point, is the basis of the coagulating and aggregating step of the present invention.

Whey or serum proteins also are present in milk, and typically are found in the liquid left after the coagulated and aggregated caseins are removed from the milk. These proteins represent a rather diverse group including $\alpha$-lactalbumin, $\beta$-lactoglobulin, bovine (blood) serum albumin, immunoglobulins, and small molecular weight peptides derived by proteolysis of some of the caseins. All of the proteins named above have been isolated, and have at least partially been characterized. In addition, milk serum contains a number of so-called minor proteins and a number of enzymes. Other proteins and enzymes are located in the membrane of the fat globules; they amount to about 0.35 grams per kilogram of milk.

Milk has many miscellaneous components. For example, all vitamins are present. Further, as analytical techniques improve, more components are being identified. The understanding of the structure of milk is provided in this specification because it is believed that the principles and unique features of the present invention can be better understood and discussed with a working knowledge of the materials which comprise the present invention.

B. The Production of Milk: Skim and Lowfat Milk Compared to Whole Milk

Raw milk is obtained from the secretion of mammary glands by mammals. Typically, raw milk is not the milk product which most individuals consume. Raw milk is first processed in dairy plants through a number of steps.

One step of the process of milk production is pasteurization. Low-temperature, long-time pasteurization (e.g., 30 minutes at 63° C.) and high-temperature, short-time pasteurization (e.g., 15 seconds at 72° C.) are milk treatments that kill most microorganisms and inactivate some enzymes, but do not cause many other changes. Higher temperature pasteurization (e.g., 1.0 second at 89° C., although the conditions vary widely in the art) is more intense; all vegetative microorganisms are killed, most enzymes are inactivated, part of the whey proteins can become denatured, and the -SH groups can become exposed.

Complete sterilization (e.g., 20 minutes at 118°C.) is meant to kill all microorganisms, including spores; inactivate all enzymes; cause numerous chemical changes, such as browning reactions; and form formic acid. Ultra-high temperature ("UHT") heating (e.g., at or above 138° C. for a few seconds) is meant to commercially sterilize milk while minimizing chemical changes, even though some enzymes are not inactivated fully.

Another step in the production of milk typically involves the use of a cream separator. The cream separator is a flow-through centrifuge which is used to separate the milk into an essentially fat-free portion (skim milk) and a fat-rich portion (cream).

Cream consists of a concentration of the fat in milk, wherein the fat mainly exists as globules protected by a membrane. As such, cream can have a variety of compositions and is normally defined according to fat content or function. The physico-chemical properties of cream are very much influenced by the state of dispersion of the milkfat globules and the globule membrane which surrounds them.

As an alternative to centrifugally separating the milk, the milk may also be separated by relying on the density difference between the milkfat in the globules and the aqueous phase in which they are dispersed. If milk is allowed to stand, fat rises, and the familiar process of "creaming" is observed with a fat-rich fraction collecting at the surface above the skim milk.

It is known that by mixing skim milk and cream, milk may be standardized to a desired fat content to produce the milk products which are commonly referred to as "1%," "2%," and "whole milk." After milk is standardized, the fat globules of milk may be broken up into very small particles (fat globules) by forcing them through special valves under high pressure (i.e., homogenization). Homogenization of milk reduces the creaming process such that the fat globules do not accumulate at the surface of the milk. All sterilized milks or, more generally, all long-life liquid milk products, are homogenized in practice.

C. Texturizing Milk Products

According to the present invention, the textured skim or lowfat milk composition is produced by treating milk with a coagulant to aggregate the proteins in the milk. Preferably, skim milk is treated with a coagulant to aggregate the proteins in the skim milk such that the skim milk becomes characterized by a texture. According to one embodiment of the present invention, the textured milk product is produced by treating skim milk with rennet to aggregate the casein in the milk. 1% and 2% milks may also be treated within the scope of the present invention although the greatest effect of the present invention can be seen with skim milk. The term "lowfat milk" refers to 1% and 2% milks.

Casein exists in milk in complex micelles which consist of casein molecules, calcium, inorganic phosphate and citrate. The micelles are roughly spherical particles, mostly 0.02 to 0.30 $\mu$m in diameter. The casein micelles also contain inorganic matter, mainly calcium phosphate, in a concentration of about 8 grams per 100 grams casein. The particles are voluminous, holding more water than casein. Finally, they contain small quantities of some other proteins, such as the milk enzymes, lipase and plasmin, and part of the proteosepeptone.

It has been found that the introduction of rennet to a skim or lowfat milk leads to the aggregation of the micelles. The rennet enzyme specifically cleaves one of the bonds in k-casein, releasing a glycomacropeptide. This action destabilizes the casein micelles such that they begin to coagulate and aggregate.

The most used preparation is calf rennet. However, although calf rennet is the preferred type of coagulating enzyme, it should be understood that many different proteolytic enzymes are able to lead to the aggregation of the micelles within the scope of the present invention. The different types of coagulants which are routinely used to aggregate the proteins in the skim milk are quite diverse. For example, various different proteolytic enzymes are available such as microbial rennets (from *Mucor miehei, Mucor pusillus, Endothia parasitica,* Bacillus spp., Aspergilllus, spp.), vegetable (plant) rennets, and other proteolytic enzymes known to those skilled in the art. What is important is that any enzyme can be employed which is capable of coagulating milk by acting on caseins without destroying the milk's suitability for human consumption. For the sake of simplicity, however, calf rennet will be referred to most often as the coagulating enzyme.

The active principle of calf rennet is the endopeptidase chymosin. Chymosin, having a molecular weight 30,700, is readily soluble in water. Chymosin hydrolyzes protein molecules into large peptides. Chymosin (as well as many other endopeptidases) splits particularly the Phe-Met bond of the k-casein. In the preferred embodiment of the present invention, preferably, in the range from about 20% to about 60% of the k-casein in the textured milk product is split before heating. It is known that at least 60% of the k-casein must be split in order for aggregation to occur. However while the milk is being heated, more of the k-casein is split. Therefore, although only 20% of the k-casein may be split before heating, the splitting continues during heating so that the amount of k-casein split eventually reaches 60%, and aggregation begins.

The splitting of the k-casein by the chymosin can be a relatively quick reaction. Small peptides containing the same bond also are split, though the reaction is much slower than on k-casein; the rate increases as the peptide is a larger portion of the k-casein molecule.

As indicated earlier, k-casein is split into para-k-casein and a caseinomacropeptide. (The latter is thus identical to the whey proteose, at least when only chymosin acts for a short time at milk pH.) The two polypeptides have very different properties. The para-k-casein is insoluble in milk serum and in the absence of $Ca^{+2}$ but it can be kept in dispersion by the other caseins. The caseinomacropeptide is very soluble, and does not associate; it is present in whey in an extended conformation, almost as a random coil. The caseinomacropeptide is heterogeneous because of the variation in glucide content.

Although the aggregation of the casein micelles is an important step in the production of the textured milk product, it must be understood that the aggregation should not be allowed to progress to the stage of gel formation, as is experienced with the production of cheeses. Cheese production involves the formation of a network by the para-k-casein micelle aggregates which have an irregular and elongated shape. As soon as a three-dimensional network forms throughout the milk, it becomes a gel or, to use a common term, a "curd".

Even after formation of the gel network, many more bonds between micelles can be formed in principle, because a much more compact packing of the micelles is possible. When this occurs, liquid is expelled from the gel, a process called "syneresis". Moisture content of the curds after syneresis depends primarily on temperature, pH, pressure gradients applied, and fat content. In practice, syneresis usually is stopped at the desired level by lowering the temperature.

In the present invention, syneresis does not occur. Moreover, a three-dimensional network does not form throughout the milk to form a gel or curd. Instead, the flocculating paracasein micelles are only allowed to form the small aggregates, and it is the presence of these small aggregates which provide the textured quality to the treated skim or lowfat milk product.

Various factors affect the production of the textured milk product. Some of these factors include: (1) the temperature of the skim or lowfat milk; (2) the amount of enzyme initially present in the skim or lowfat milk; (3) the time the enzyme is allowed to act on the caseins before the enzyme is deactivated; (4) and the amount of milk used.

With regard to the temperature of the skim or lowfat milk, a heat treatment of greater intensity than low pasteurization causes an increase in rennet activity. Using decreased temperature causes a decrease in rennet activity. An increase in rennet activity reduces the incubation period, i.e., the time with which a milk sample, inoculated with rennet, is required to stand before a sufficiently high temperature must be delivered to deactivate the rennet. It should be remembered, however, that if the heat treatment is too severe, the rennet is denatured and rennet activity is discontinued.

With regard to the amount of the enzyme, a higher amount of enzyme introduced into the milk sample causes a rate increase in the aggregation occurring in the milk sample. This reduces the necessary incubation period. Conversely, a lower amount of enzyme introduced into the milk sample causes a decrease in the aggregation and thereby increases the necessary incubation period.

The longer the period of time the enzyme is allowed to react with the caseins in the milk sample, the greater the aggregation of the caseins in the milk sample to arrive at a textured milk product. The less time the enzyme is allowed to react with the casein in the milk sample, the less aggregation occurs.

Further, the greater the milk-to-enzyme ratio, the longer it takes for the enzymes to react with all of the caseins present in the milk sample. The smaller the milk-to-enzyme ratio, a shorter time period is necessary for reaction of the enzymes with the caseins.

It can be seen that the factors affecting the process are all interrelated and can be altered in response to alterations of each other factor. It is a simply a matter of routine experimentation by one with ordinary skill in the art to discover the various possible combinations.

D. Textured Milk Processing System

The complete milk processing system of the present invention, wherein skim or lowfat milk is textured, is outlined in FIG. 1. The milk processing system comprises a series of pipes and vats through which the milk of the present invention is transported. The milk processing system also comprises other apparatus known to those skilled in the art to process the milk product of the present invention.

According to the preferred embodiment of the present invention a quantity of milk is initially cooled if needed, to about 40° F. (about 4° C.). (Before the enzyme unculation, pasteurizing, ultrapasteurizing and homogenizing the milk can optionally be performed if desired.) After the milk is cooled, the milk is inoculated with the coagulating enzyme. The milk, and the coagulating enzyme used to inoculate the milk, will vary in quantity depending upon the design choice of the person manufacturing the textured milk product. In the preferred embodiment, the textured milk product is comprised of about 90 grams of rennet per 45 kilograms of milk.

The temperature of the milk at the time of inoculation is preferably about 40° F. (about 4° C.). The temperature of the milk during the period of inoculation and incubation is in the range from about 35° F. (about 2° C.) to about 50° F. (10° C.) when the reaction time is in the range from about 30 to 60 minutes. Alternatively, the temperature of the milk during the period of inoculation and incubation is in the range from about 35° F. (about 2° C.) to about 75° F. (24° C.) when the reaction time is in the range from about 10 to 90 minutes. The temperature of the milk during the period of inoculation may also be in the range from about 35° F. (about 2° C.) to about 104° F. (40° C.) when the reaction time is in the range from about 5 to 90 minutes, It must be noted that in the present invention, the factors of time, temperature and concentration share an important relationship, wherein the range of one factor is dependent upon the range of the other two factors. Therefore, many different combinations of the three factors can be successfully used.

For example, if a higher level of enzyme is used and the temperature is held constant, then the necessary reaction time will be shorter. If a lower level of enzyme is used and the temperature is held constant, then the necessary reaction time will be longer.

Similarly, if the level of enzyme is kept constant and the temperature is raised, the reaction time will decrease. If the level of enzyme is kept constant and the temperature lowered, the reaction time will increase. Further, if the level of enzyme and the reaction time are both held constant, then the temperature of the reaction can be varied. While many combinations can be used to effect the process of the present invention, the various combinations can easily be discovered by simple experimentation by those with ordinary skill in the dairy field.

The inoculation step of the present invention may further be comprised of the step of mixing the milk with the calf rennet such that the calf rennet is evenly dispersed throughout the quantity of milk. Dispersing the calf rennet throughout the quantity of milk prevents the aggregation of proteins in limited areas so that much of the skim milk continues to exhibit a watery mouthfeel to a consumer. The step of mixing may comprise blending, or stirring, the calf rennet throughout the skim or lowfat milk.

The inoculated milk is then incubated, that is, allowed to stand for a period of time. During this period of time, the calf rennet reacts with the casein in the milk to cause k-casein hydrolysis, leading to casein aggregation. As discussed previously, the aggregation of the casein by the calf rennet should not continue to such a degree that a gel is formed from the milk.

The time that the inoculated milk is allowed to stand varies depending upon the design choice of the manufacturer of the textured milk product. Preferably, the inoculated milk is allowed to stand for about 30 to about 60 minutes at a temperature of about 35° F. (about 2° C.) to about 50° F. (10° C.). In another embodiment, the inoculated milk is allowed to stand in the range from about 10 to about 90 minutes at a temperature range of about 35° F. (about 2° C.) to about 75° F. (24° C.). In still another embodiment, the inoculated milk is allowed to stand in the range from about 5 to about 90 minutes in a temperature range of about 35° F. (about 2° C.) to about 104° F. (40° C.). Again, the time the milk is allowed to stand varies with the related factors. An appropriate incubation time with the appropriate temperature can be determined by simple and routine experimentation.

In the preferred embodiment of the present invention, the inoculated milk, after it is allowed to stand for a period of time to hydrolyse and aggregate, is heated or i.e. pasteurized. The step of pasteurization is performed for a variety of reasons.

One reason for pasteurizing milk is to minimize possible health hazards arising from pathogenic microorganisms associated with milk. In the present invention, the milk is heat-treated to cause the pasteurizing effect. Pasteurization results in minimal chemical, physical, and organoleptic changes in the milk.

Another reason for pasteurizing milk, and which is an important step in the present invention, is to halt the reaction of the calf rennet with the casein in the milk. The increased temperature of the milk, represented by the pasteurization process, denatures and inactivates the calf rennet. The inactivated calf rennet is prevented from causing further aggregation of the casein in the milk, which, if allowed to continue, would form the gel which would lead to the production of cheese.

Pasteurization can be defined in different ways, based on the relationship between temperature and time. For example, high temperature-short time ("HTST") pasteurization is approximately 72° C. for about 16 seconds. Milk can also be pasteurized at about 62° C. if held at that temperature for about 30 minutes. With the present invention, pasteurization at 72° C. for about 16 seconds is preferred, although pasteurization at 63° C. for about 30 minutes can also be used. The necessary times and temperatures are those that create conditions necessary to destroy the enzyme after the enzyme is finished. Any temperature above 72° C. (for about 16 seconds) up to about 142°C. (for about six seconds) will create these conditions.

As indicated previously, a high milk-to-enzymeration will considerably slow the aggregation of the casein in the milk product. Therefore, it can be understood that instead of pasteurizing the inoculated milk to halt the aggregation of casein by the enzyme, one may introduce a large quantity of non-inoculated milk into the inoculated milk to substantially halt the aggregation of casein by the enzyme since there will be a high milk-to-enzyme ratio. Such a procedure, which essentially involves diluting the concentration of the enzyme in the milk, may be necessary when heating of the milk cannot be immediately accomplished.

The method of producing the textured skim or lowfat milk product within the scope of the present invention also includes the step of storing the pasteurized milk until such time as the textured milk product is purchased by a consumer. In one embodiment of the present invention, the pasteurized milk is placed in a holding tank. In another embodiment of the present invention, the pasteurized milk is concentrated into a powdered form in order to store the textured milk product. The powdered milk product can be reconstituted by the addition of water.

The method of storing the textured milk product most often comprises the step of cooling the pasteurized milk to an appropriate refrigeration temperature. The reduction in the temperature of the milk product decreases the growth rate of any microorganisms not killed or deactivated by the pasteurization step. Most milk products are cooled to a temperature in the range from about 35° F. (about 2° C.) to about 40° F. (about 4° C.).

E. Physical Characteristics of the Textured Milk Product

The textured skim or lowfat milk product can be characterized by various physical traits. As indicated previously, microscopic examination of the textured skim milk indicates aggregates of casein which are elongated and irregularly shaped. Nevertheless, the aggregates of casein have been found to be a variety of additional shapes and sizes which may be known to those skilled in the art.

Typically, the aggregates of casein may have a width of about 0.5-10 micrometers and a length of about 0.5-10 micrometers. Most of the aggregates will usually be in the range from about 1-3 micrometers.

As the skim or low fat milk is textured, a color change occurs which can be measured. This color change can indicate the change that occurs in the textured skim or lowfat milk.

A reflectance colorimeter measures the light that reflects from a food sample. The reflected light is detected and is expressed as a three (3) part color measurement. The color ranges are: $L^*$ which measures between black (zero value) to white (100 value); $a^*$ which measures between green (negative 80 value) to red (positive 100 value); $b^*$ which measures between blue (negative 80 value) to yellow (positive 70 value). The color of textured skim milk and milk with a fat content are most critically evaluated using the $L^*$ and $b^*$ values.

The textured milk product can be characterized by the increased white and decreased bluish colors of the textured milk product. The $L^*$ value of the textured milk product is preferably in the range from about 55 to 65, indicating an increased whiteness to the textured milk product. Untreated skim milk (no enzyme treatment) usually has an $L^*$ value of about 45 to 50, indicating less whiteness to the normal skim milk. Milk with a fat content (for example, 2% milk) has an $L^*$ value of approximately 65 to 75, indicating significant whiteness value.

The $b^*$ value of the textured milk product using skim milk is preferably in the range from about $-5$ (negative 5) to about $-2$ (negative 2), indicating a decreased bluish color to the textured milk product. Untreated skim milk (no enzyme treatment) usually has a $b^*$ value from about $-10$ (negative 10), to about $-8$ (negative 8) indicating more bluish hue to the normal skim milk. Milk with a fat content (for example, 2% milk) has a $b^*$ value of approximately $-7$ (negative 7) to $-4$ (negative 4), indicating less bluish hue to the fat-containing milk.

EXAMPLES

The use of the methods for producing a textured milk product within the scope of the present invention will be further clarified by a consideration of the following examples, which are intended to be purely exemplary of the use of the invention and should not be viewed as a limitation on any claimed embodiment.

EXAMPLE 1

Sensory evaluation tests by milk consumer taste panelists were conducted to determine the perceived creaminess mouthfeel between the milk of the textured skim milk product and 2% milk. These milks were also compared in sensory tests to normal skim milk, i.e. nonenzyme treated. The comparison test was performed by placing three pairs of two test milk samples in each pair in front of test subjects. The two test milk samples were paired as: normal skim milk vs. textured skim milk; normal skim milk vs. normal 2% milk; and textured skim milk vs. normal 2% milk.

The test subjects were asked to evaluate the test milk samples in each pair and indicate on the questionnaire ,which test milk sample of the pair had the creamier mouthfeel. Seventy percent (70%) of respondents indicated the textured skim milk product had a creamier mouthfeel when compared to normal skim milk. Sixty-three percent (63%) of respondents indicated the normal 2% milk had a creamier mouthfeel when compared to normal skim milk. Seventy-three percent (73%) of respondents indicated the textured skim milk product had a creamier mouthfeel when compared to normal 2% milk.

The results of the test indicated that milk consumers are unlikely to be able to differentiate between the textured skim milk product of the present invention and normal 2% milk in terms of the body and mouthfeel of the milk product. Almost always, a milk consumer is able to differentiate between skim milk and 2% milk when compared side-by-side in a taste comparison due to the difference in milkfat content. Despite the lower milkfat content of the textured skim milk product, the data indicate that its mouthfeel was perceived as creamier than either normal skim milk or normal 2% milk.

EXAMPLE 2

Six gallons (51.6 pounds or 23.4 kilograms) of skim milk., having a fat content of approximately 0.3%, was obtained at a temperature of about 40° F. (about 4° C.). To the skim milk, about 4.6 grams of single-strength calf rennet (diluted 1:40 in cold water) was introduced. The composition was then mixed by stirring.

After approximately 18 to 20 minutes of enzyme action, the inoculated skim milk was heat treated. The enzyme-treated skim milk was preheated to 164° F. (about 73° C.) and then ultra-high temperature treated at 285° F. (about 141° C.) and held for 4 seconds. The heat treatment of the inoculated skim milk substantially inactivated the calf rennet in the skim milk.

The pasteurized skim milk was then placed under refrigerator conditions where it was stored until consumption. The temperature of the holding tank was about 40° F. (about 4° C.). Consumption of the processed skim milk revealed that the milk tasted similar to 2% milk in spite of the fact that the skim milk contained substantially less milkfat than the 2% milk.

It must be noted that all milk samples must be pasteurized at some time during the process, even if the milk is eventually UHT processed. Within the scope of the present invention, generally skim milk is pasteurized and then cooled prior to inoculation with the appropriate enzyme level. The inoculated milk is allowed to react with the enzyme at reduced temperature (e.g. about 4° C.). The inoculated and textured skim milk is then heat-treated (preferably pasteurized) again in order to inactivate the enzyme. The second heat treatment can also be a UHT treatment.

It is also feasible to UHT process the milk prior to enzyme inoculation. The UHT-treated milk is cooled and allowed to react with the enzyme at 40° F. (about 4° C.). The textured skim milk is then pasteurized to inactivate the enzyme.

EXAMPLE 3

A textured milk product is produced according to the procedure of Example 2, except that 1% milk is processed according to the methods of the present invention to arrive at a more textured milk product instead of skim milk. This example is important to show that different standards of milk may be characterized by greater texture and improved quality of taste in spite of low milkfat content. Therefore, 1% milk may taste like 2% milk or even whole milk.

EXAMPLE 4

A textured milk product is produced according to the procedure of Example 2, except that 2% milk is processed according to the methods of the present invention to arrive at a more textured milk product instead of skim milk. This example is important to further show that different standards of milk may be characterized by greater texture and improved quality of taste in spite of low milk-fat content. Therefore, 2% milk may taste like whole milk.

EXAMPLES 5–10

The following examples illustrate experiments which were conducted to determine the color change(s) occurring in the textured skim milk of the present invention. The color of untreated skim milk was compared to the colors of treated skim milk, 1% milk, and 2% milk. Reference should be made to the Figures when necessary. The numbers at the top (or bottom) of each bar in the Figures indicate average value ± standard deviation.

EXAMPLE 5

Untreated samples one hundred gallons of milk (860 pounds) of skim milk (approximate fat content of 0.4%) was obtained, preheated to 140° F. (60° C.) and held for 25 seconds. Sample 1 ("Skim-1") was homogenized at 800 psi in the first stage and 200 psi in the second stage. Sample 2 ("Skim-2") was homogenized at 2,000 psi in the first stage and 500 psi in the second stage. The samples were cooled to approximately 45° F. (7° C.) by plate heat exchange immediately following the heat and homogenization treatments. These samples 1 and 2 (FIG. 2) represent the pre-enzyme, preheat treatment ("untreated") samples.

Treated samples

Calf rennet (77.4 ml diluted 1:40 in cold water) was then added to the 860 pounds of skim milk at approximately 45° F. (7° C.) for one hour.

The enzyme-treated skim milk was then heated to 170° F. (77° C.) and held for 25 seconds to inactivate the enzyme. Three (3) sets of samples were generated. Samples 1A and 2A were not homogenized following the 77° C. heat treatment. Samples 1B and 2B were homogenized at 800 psi in the first stage and 200 psi in the second stage. Samples 1C and 2C were homogenized at 2,000 psi in the first stage and 500 psi in the second stage. All samples were cooled to approximately 45° F. (7° C.) by plate heat exchange immediately following the heat and homogenization treatments. The samples were refrigerated at 7° C.

Figure 2:
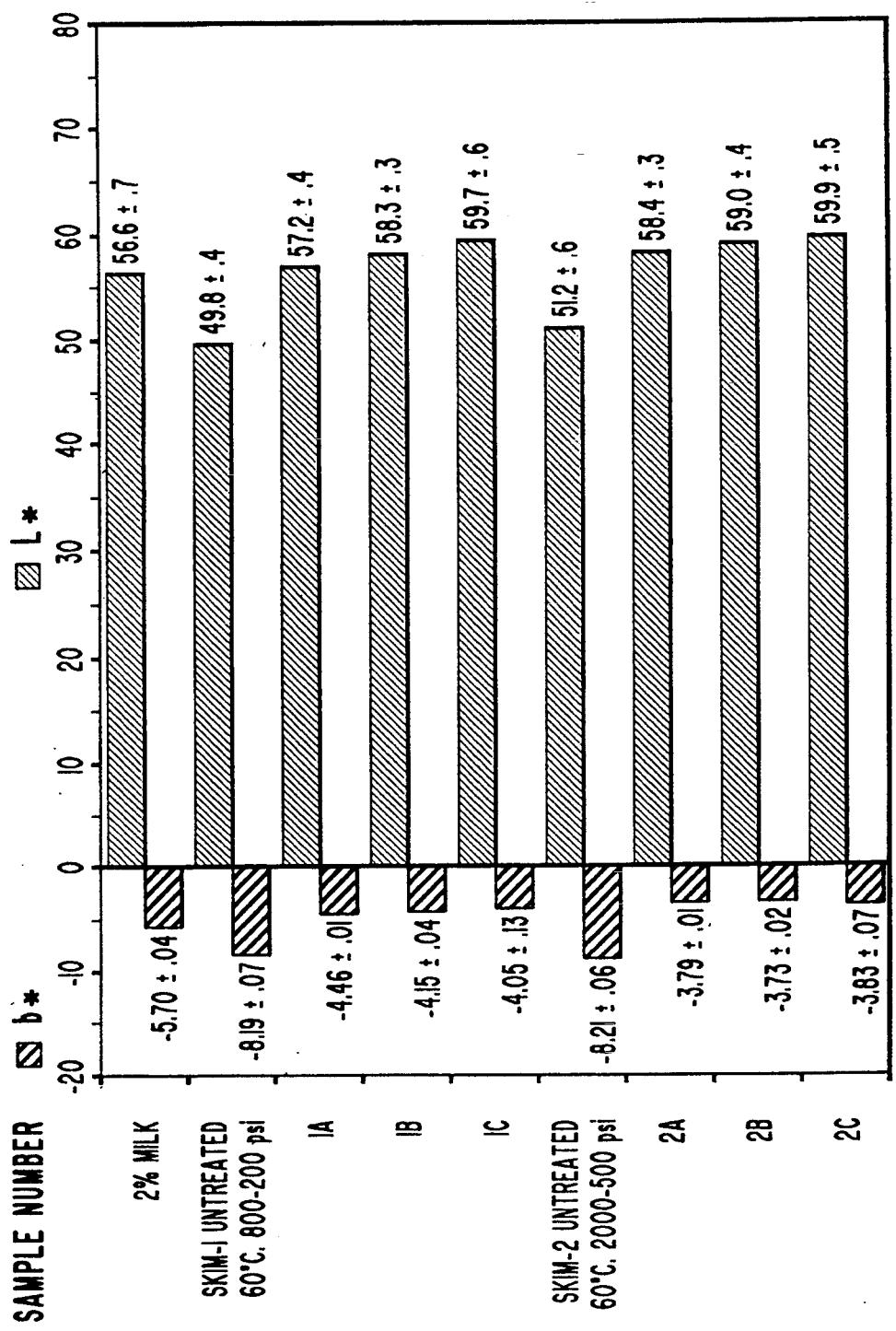
FIG. 2. is a graph illustrating L* and b* values for experiments performed in Example 5.

Color measurements were performed on an OMNIS-PEC ™ Reflectance Colorimeter manufactured by Wescor, Inc., Logan, Utah. The L* value, which measures between black (zero value) to white (100 value), and the b* value, which measures between blue (negative 80 value) to yellow (positive 70 value), were measured. The resulting data are illustrated in FIG. 2. FIG. 2 illustrates the L* and b* values of the samples 1A, 1B, and 1C, and 2A, 2B, and 2C as compared with untreated skim milk samples ("Skim-1" and "Skim-2") and 2% milk.

It can be seen from reference to FIG. 2 that the untreated skim milk samples (those not receiving any enzyme treatment) have a reduced whiteness value. These samples received the preheat treatment and homogenization pressures treatment without any enzyme addition.

Samples 1A, 1B, 1C, 2A, 2B, and 2C all showed an increase in the whiteness value (a higher L* value) as a result of the enzyme treatment. In all samples, the enzyme treatment and combined heat/homogenization treatments resulted in L* values higher than the 2% milk sample.

As seen from reference to FIG. 2, the untreated skim milk samples ("Skim-1" and "Skim-2"), have a lower b* value (i.e., a higher blue value—the more negative the number the more blue hue to the food sample).

Samples 1A, 1B, 1C, 2A, 2B, and 2C all showed a decrease in the blue value as a result of the enzyme treatment. In all samples, the enzyme treatment and combined heat/homogenization treatments resulted in less negative b. values than the 2% milk sample.

EXAMPLE 6

Experiments were performed using similar processes as described in Example 5. The untreated samples ("Skim-3" and "Skim-4") were processed similarly as to "Skim-1" and "Skim-2"in Example 5 except the pre-enzyme, preheat temperature was 170° F. (77° C.). Treated samples 3A, 3B, and 3C were processed similarly to samples 1A, 1B, and 1C except the pre-enzyme, preheat temperature was 170° F. (77° C.). Treated samples 4A, 4B, and 4C were processed similarly to samples 2A, 2B, and 2C except the pre-enzyme, preheat temperatures was 170° F. (77° C.).

Figure 3:
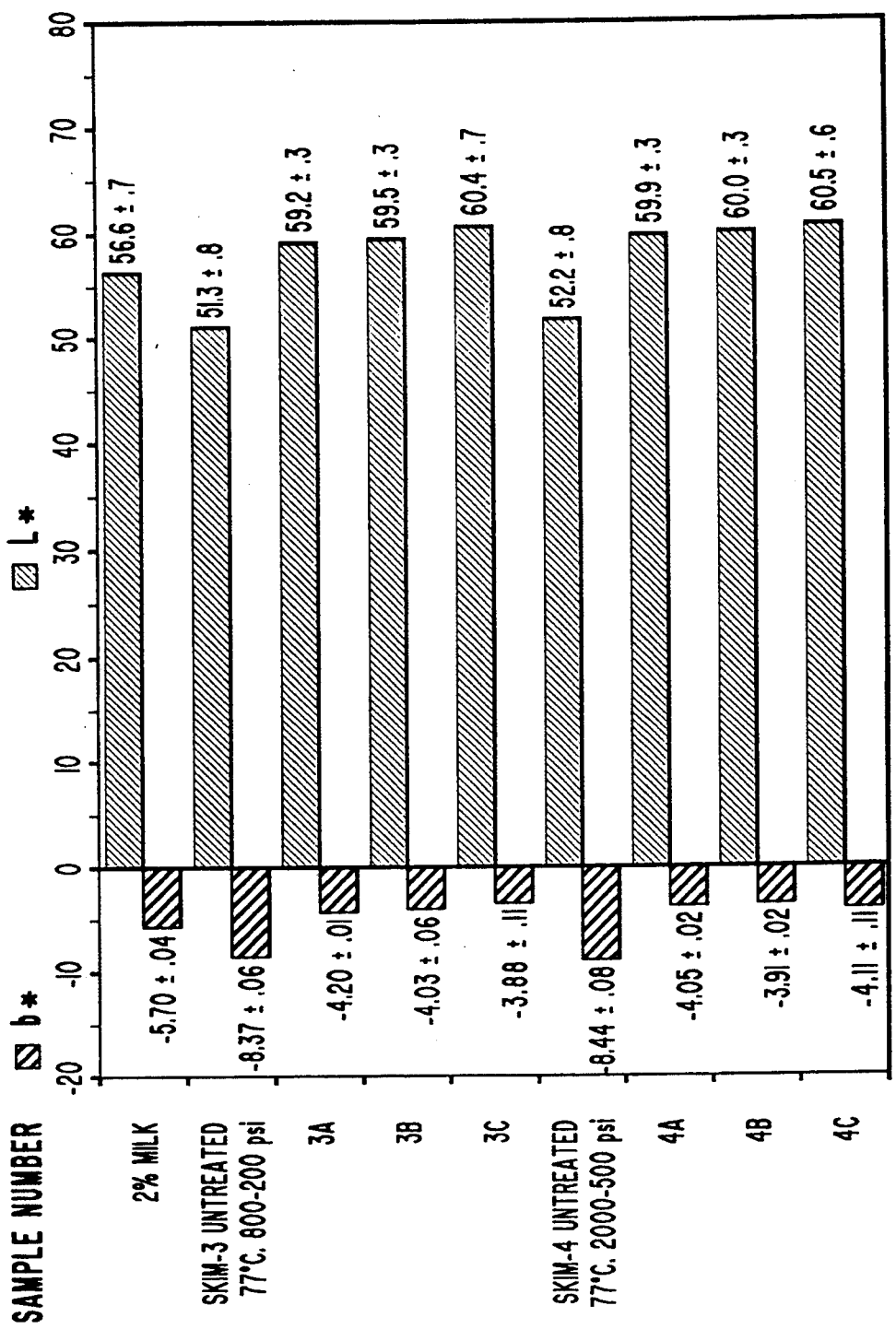
FIG. 3 is a graph illustrating L* and b* values for experiments performed in Example 6.

The results of the experiments are illustrated in FIG. 3. Enzyme treatment of the skim milks (samples 3A, 3B, and 3C and 4A, 4B, and 4C) caused the L* value to increase and the b* value to become less negative compared with the untreated skim milks ("Skim-3" and "Skim-4") and the 2% milk.

EXAMPLE 7

Experiments were performed using similar processes as described in Example 5. The untreated sample ("Skim-5") was processed similarly as to "Skim-1" in Example 5 except the. pre-enzyme, preheat temperature was 200° F. (about 93° C.). Treated samples 5A, 5B, and 5C were processed similarly to samples 1A, 1B, and 1C except the pre-enzyme, preheat temperature was 200° F. (about 93°C.).

Figure 4:
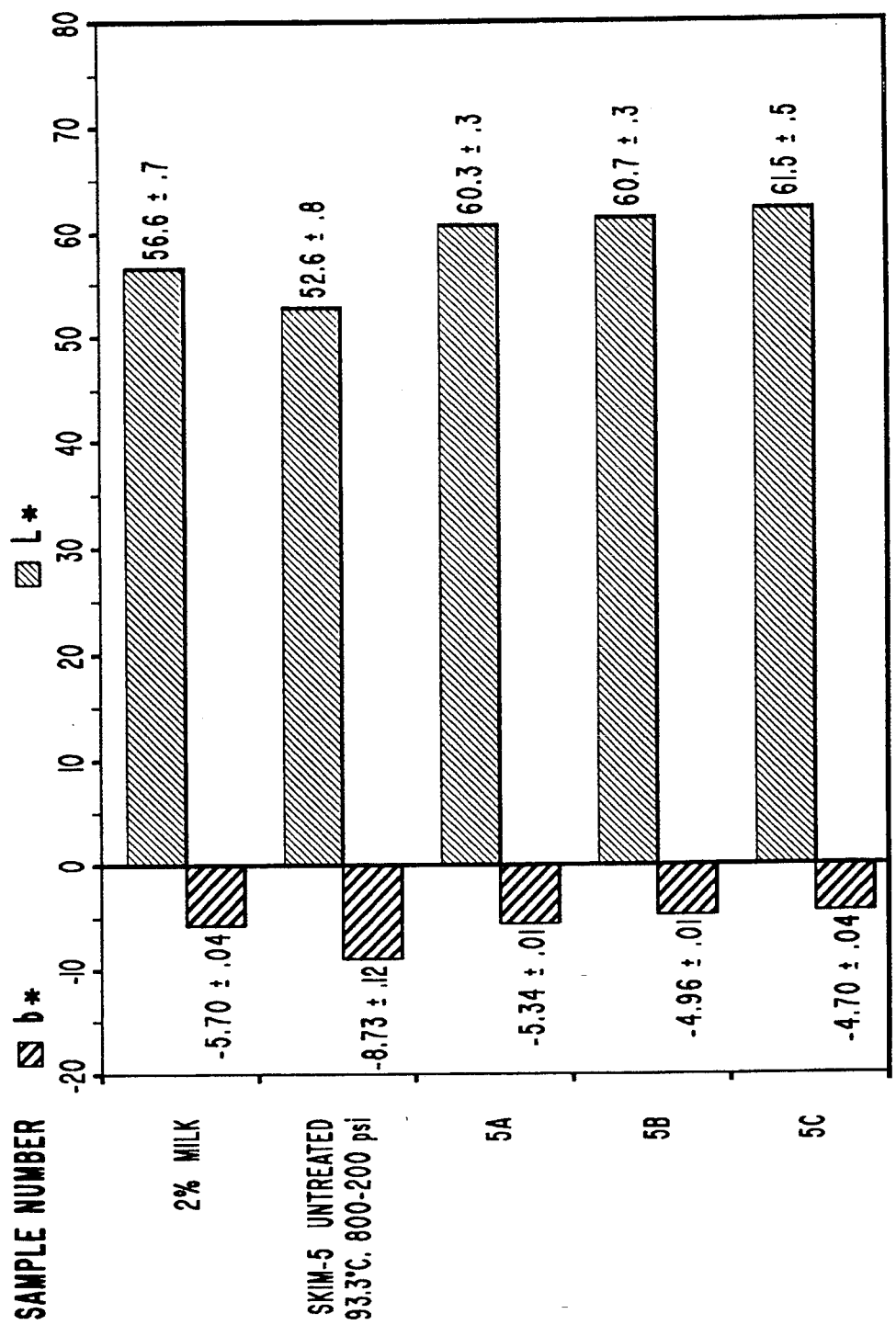
FIG. 4 is a graph illustrating L* and b* values for experiments performed in Example 7.

The results of the experiments are illustrated in FIG. 4. Enzyme treatment of the skim milk (samples 5A, 5B, and 5C) caused the L* value to increase and the b* value to become less negative compared with the untreated skim milks ("Skim-5") and the 2% milk.

EXAMPLE 8

Experiments were performed using the same basic processes as described in Example 5, except that 1% and 2% milks were treated. Comparison of experimental results were made with untreated 1% milk sample ("Milk-1") and untreated 2% milk sample ("Milk-2") and whole milk.

Untreated Samples:

One hundred gallons (860 pounds) of 1% and 2% milks were obtained, preheated to 140° F. (60° C.) and held for 25 seconds. Sample 1 ("Milk-1") was homogenized at 2,000 psi in the first stage and 500 psi in the second stage. Sample 2 ("Milk-2") was homogenized at 2,000 psi in the first stage and 500 psi in the second stage. The samples were cooled to approximately 45° F. (7° C.) by plate heat exchange immediately following the heat and homogenization treatments. These samples 1 and 2 (FIG. 5) represent the pre-enzyme, preheat treatment ("untreated") samples.

Treated samples:

calf rennet (77.4 ml diluted 1:40 in cold water) was then added to the 860 pounds of 1% and 2% milks at approximately 45° F. (7° C.) for one hour.

The enzyme-treated milks were then heated to 170° F. (77° C.) and held for 25 seconds to inactivate the enzyme. Three (3) sets of samples were generated. Samples 1A and 2A were not homogenized following the 170° F. (77° C.) heat treatment. Samples 1B and 2B were homogenized at 800 psi in the first stage: and 200 psi in the second stage. Samples 1C and 2C were homogenized at 2000 psi in the first stage and 500 psi in the second stage. All samples were cooled to approximately 45° F. (7° C.) by plate heat exchange immediately following the heat and homogenization treatments. The samples were refrigerated at 45° F. (7° C.).

Figure 5:
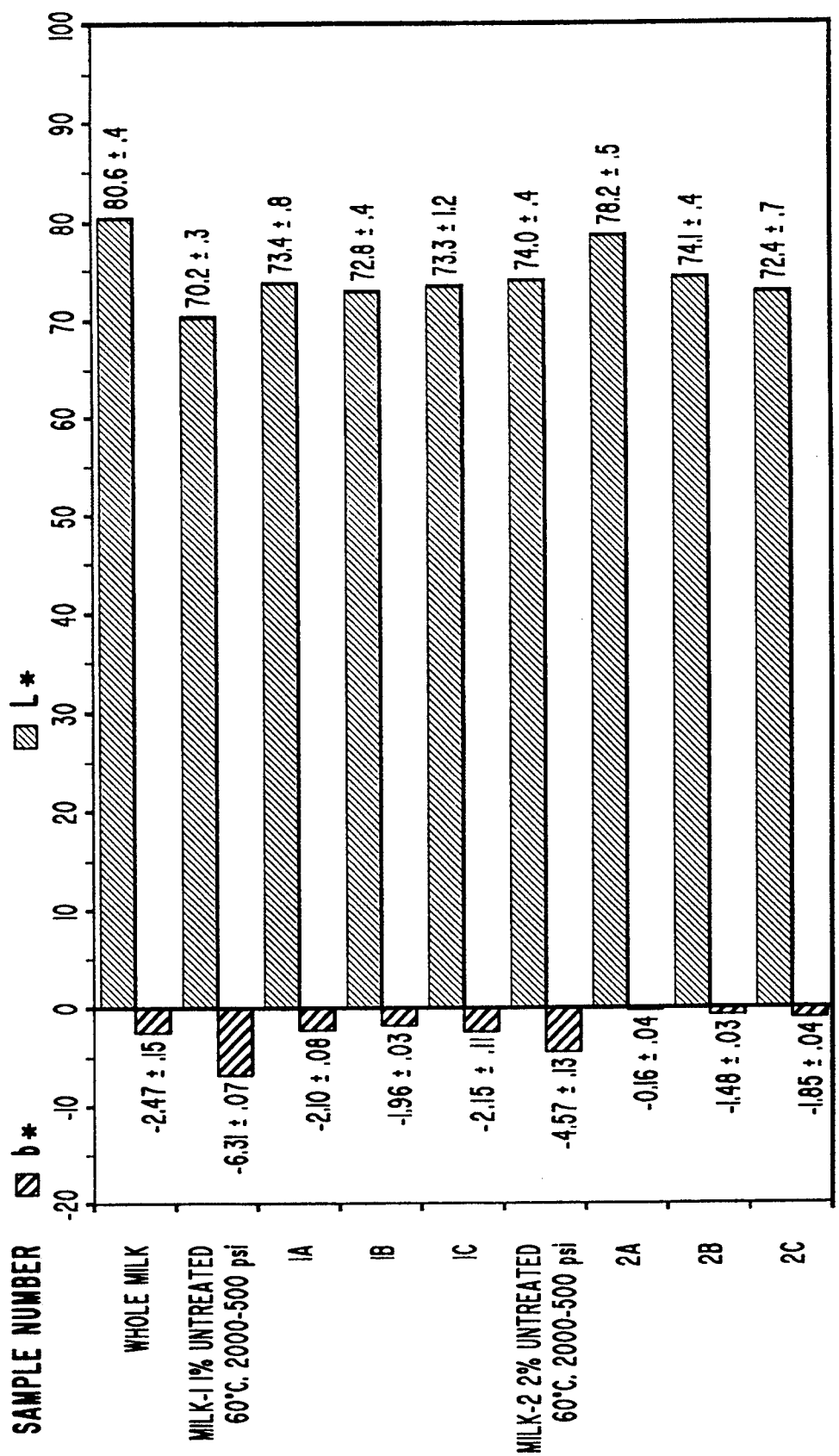
FIG. 5 is a graph illustrating L* and b* values for experiments performed in Example 8.

Color measurements were performed by reflectance colorimetry. The L* value, which measures between black (zero value) to white (100 value), and the b* value, which measures between blue (negative 80 value) to yellow (positive 70 value), were measured. The resulting data are illustrated in FIG. 5. FIG. 5 illustrated the L* and b* values of the samples 1A, 1B, and 1C, and 2A, 2B, and 2C as compared with untreated 1% milk sample ("Milk-1") and untreated 2% milk sample ("Milk-2") and whole milk.

It can be seen from reference to FIG. 5 that the untreated 1% and 2% milk samples (those not receiving any enzyme treatment) have a reduced whiteness value compared with the respective enzyme-treated samples.

Samples 1A, 1B, 1C, 2A, 2B, and 2C all showed an increase in the whiteness value (a higher L* value) as a result of the it enzyme treatment. In all samples, the enzyme treatment and combined heat/homogenization treatments resulted in L* values higher than their untreated counterpart milk sample.

As seen from reference to FIG. 5, the untreated 1% milk sample ("Milk-1") and untreated 2% milk sample ("Milk-2") had a lower b* value (i.e., a higher blue value—the more negative the number, the more blue hue to the food sample).

Samples 1A, 1B, 1C, 2A, 2B, and 2C all showed a decrease in the blue value as a result of the enzyme treatment. In all samples, the enzyme treatment and combined heat/homogenization treatments resulted in less negative b* values than the untreated counterpart milk sample and compared with the whole milk.

EXAMPLE 9

Experiments were performed using similar processes as described in Example 8. The untreated 1% and 2% milk samples ("Milk-3" and "Milk-4," respectively) were processed similarly as to "Milk-1" and "Milk-2" in Example 8 except the pre-enzyme, preheat temperature was 170° F. (77° C.). Treated samples 3A, 3B, and 3C were processed similarly to samples 1A, 1B, and 1C in Example 8 except that the pre-enzyme, preheat temperature was 170° F. (77° C.). Treated samples 4A, 4B, and 4C were processed similarly to samples 2A, 2B, and 2C in Example 8 except the pre-enzyme, preheat temperature was 170° F. (77C).

Figure 6:
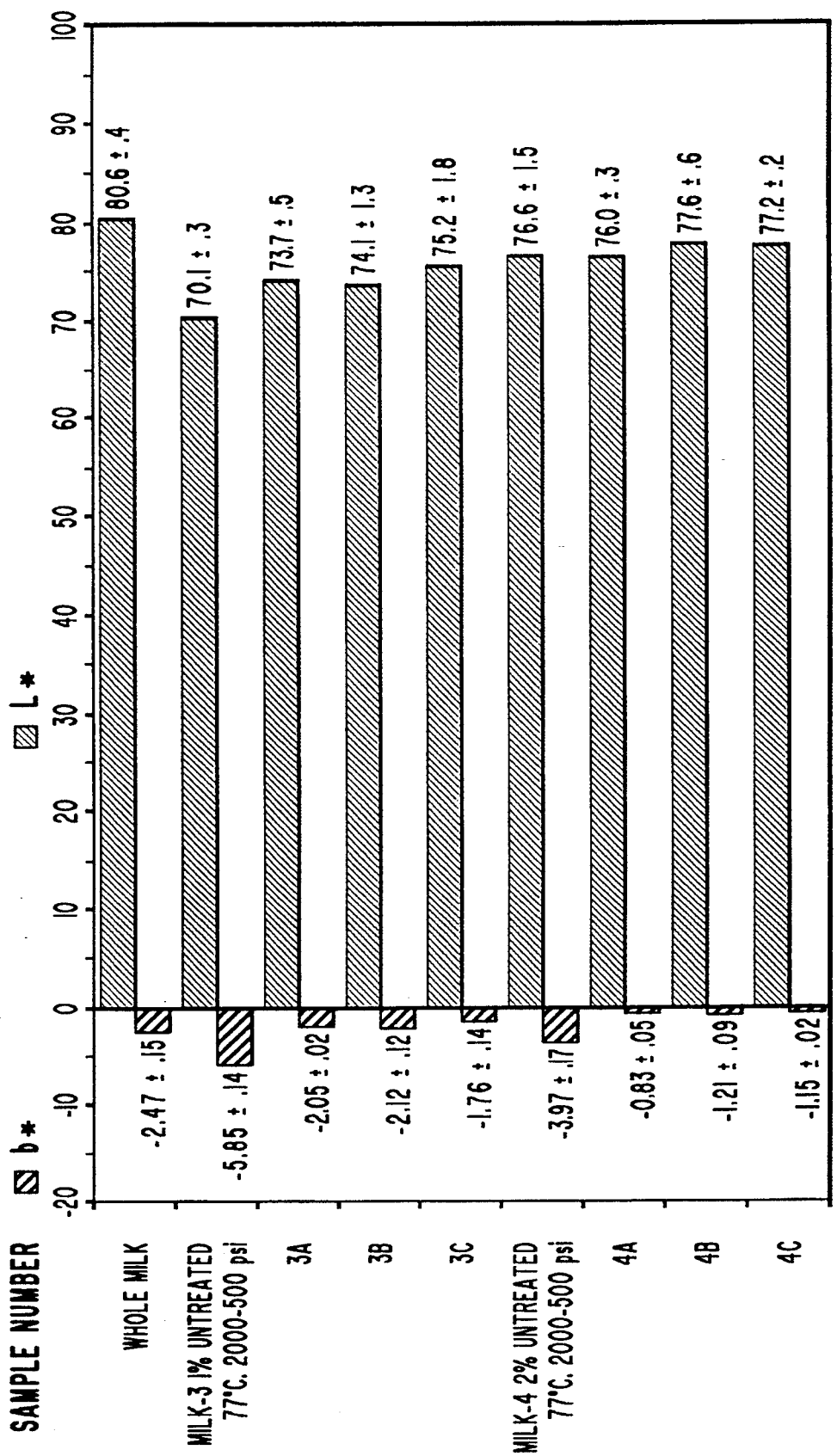
FIG. 6 is a graph illustrating L* and b* values for experiments performed in Example 9.

The results of the experiments are illustrated in FIG. 6. Enzyme treatment of 1% milks (samples 3A, 3B, and 3C) and of the 2% milk (4A, 4B, and 4C) caused the L* value to increase compared with the untreated counterpart milk sample and the b* value to become less negative compared with the untreated counterpart milks ("Milk-3" and "Milk-4") and compared with the whole milk.

EXAMPLE 10

Experiments were performed using similar processes as described in Example 8. The untreated 1% and 2% milk sample ("Milk-5" and "Milk-6") were processed similarly as to "Milk-1" and "Milk-2" in Example 8 except that the pre-enzyme, preheat temperature was 200° F. (about 93° C.). Treated samples 5A, 5B, and 5C were processed similarly to samples 1A, 1B, and 1C in Example 8 except the pre-enzyme, preheat temperature was 200° F. (about 93° C.). Treated samples 6A, 6B, and 6C were processed similarly to samples 2A, 2B, and 2C in Example 8 except that the pre-enzyme, preheat temperature was 200°°F. (about 93° C.).

Figure 7:
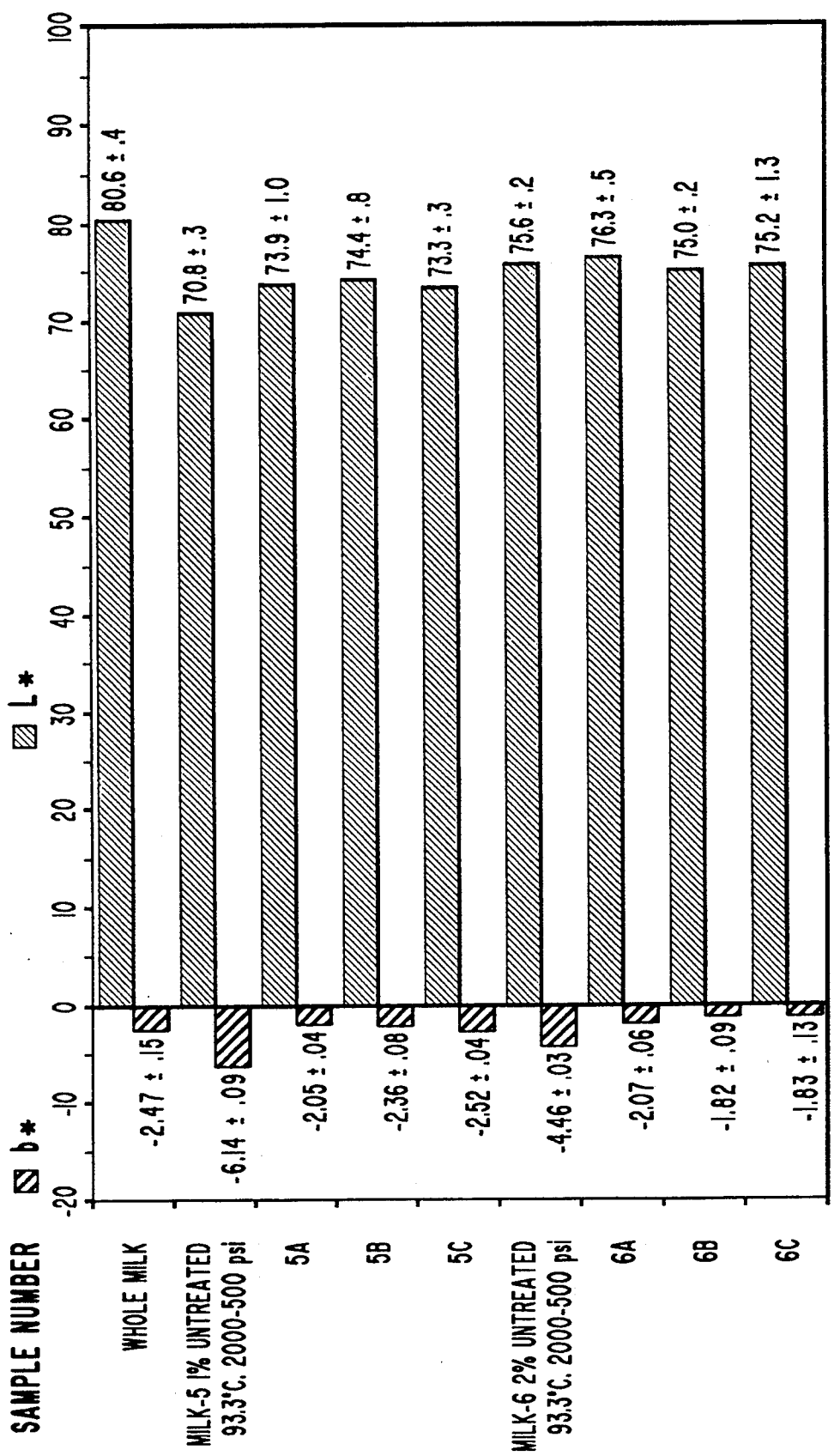
FIG. 7 is a graph illustrating L* and b* values for experiments performed in Example 10.
Figure 8:
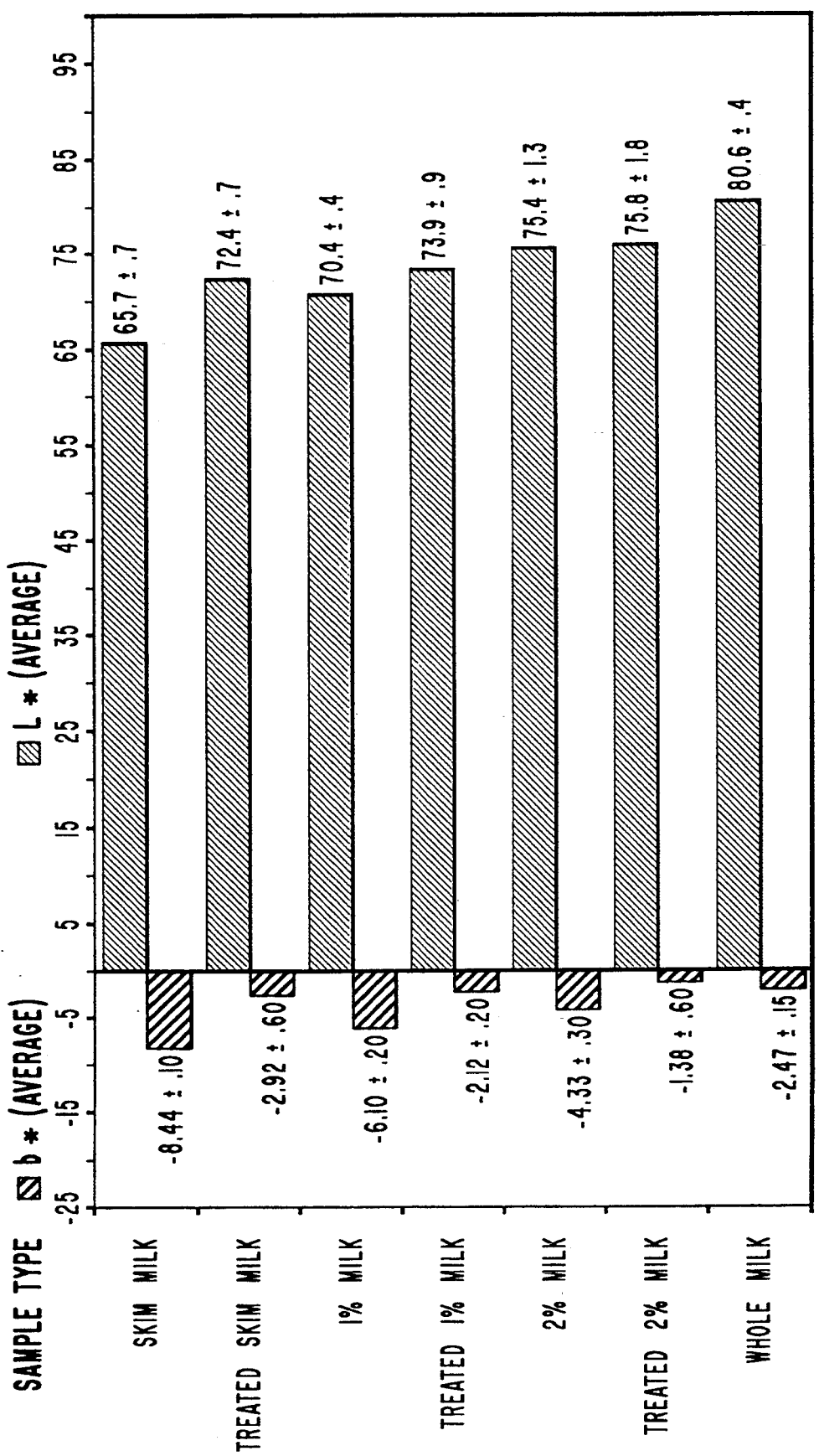
FIG. 8 is a graph illustrating average L* and b* values for experiments performed in Examples 5 to 10.

The results of the experiments are illustrated in FIG. 7. Enzyme treatment of the 1% milks (samples 5A, 5B, and 5C) and of the 2% milk (6A, 6B, and 6C) caused the L* value to increase compared with the untreated counterpart milk sample and the b* value to become less negative compared with the untreated counterpart milks ("Milk-5" and "Milk-6") and compared with whole milk.

It can be seen from these experiments that enzyme treatment caused a change in a color of the milks by decreasing the blueness and, for the most part, increasing the whiteness. This change in color affects the enjoyment of the skim and lowfat milks because the milks after treatment appear more like milk with higher fat content.

SUMMARY

From the foregoing, it will be appreciated that the present invention provides compositions of and methods for making skim and lowfat milk products wherein the skim and lowfat milk is textured so that individuals will believe they are drinking milk with a fat content greater than normal skim or lowfat milk, and colored so that the milk does not appear so blue and unappetizing.

The present invention also provides compositions of and methods for making a skim or lowfat milk product which fools the tongue of an individual without providing unwanted fats and without destroying taste.

The present invention further provides compositions of and methods for making a skim or lowfat milk product which is not temperature sensitive.

Still further, the present invention provides compositions of and methods for making a skim or lowfat milk product which has greater consumer acceptability due to its increased creaminess, color and mouthfeel as compared with untreated skim and lowfat milks.

Additionally, the present invention provides compositions of and methods for making a skim or lowfat milk product wherein individuals receive the health benefits from the consumption of nonfat or lowfat milk without sacrificing the enjoyment of milks with higher fat contents.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A method for manufacturing a skim milk product, the method comprising the steps of:
   (a) inoculating skim milk with a coagulating enzyme to cleave a portion of the casein in the skim milk so as to destabilize the casein;
   (b) incubating the inoculated skim milk for a period of time sufficient to allow the destabilized casein in the skim milk to form aggregates of destabilized casein so as to produce a skim milk product having a mouthfeel similar to milk having milk-fat content; and
   (c) heat treating the inoculated skim milk to inactivate substantially all of the coagulating enzyme.

2. The method for manufacturing a skim milk product as defined in claim 1, further comprising the step of pre-heat treating the skim milk before the step of inoculating the skim milk with the coagulating enzyme.

3. The method for manufacturing a skim milk product as defined in claim 1, wherein the method further comprises the step of storing the skim milk product so as to prevent the skim milk product from spoiling.

4. A method for manufacturing a skim milk product as defined in claim 1, wherein the step of incubating the inoculated skim milk comprises the step of incubating the inoculated skim milk at a temperature in the range from about 35° F. to about 50° F.

5. A method for manufacturing a skim milk product as defined in claim 1, wherein the step of incubating the inoculated skim milk comprises the step of incubating the inoculated skim milk at a temperature in the range from about 35° F. to about 75° F.

6. A method for manufacturing a skim milk product as defined in claim 1, wherein the step of incubating the inoculated skim milk comprises the step of incubating the inoculated skim milk at a temperature in the range from about 35° F. to about 104° F.

7. A method for manufacturing a skim milk product as defined in claim 4, wherein the step of incubating the inoculated skim milk comprises the step of incubating the inoculated skim milk for a period in the range from about 30 to about 60 minutes.

8. A method for manufacturing a skim milk product as defined in claim 5, wherein the step of incubating the inoculated skim milk comprises the step of incubating the inoculated skim milk for a period in the range from about 10 to about 90 minutes.

9. A method for manufacturing a skim milk product as defined in claim 6, wherein the step of incubating the inoculated skim milk comprises the step of incubating the inoculated skim milk for a period in the range from about 5 to about 90 minutes.

10. A method for manufacturing a skim milk product as defined in claim 1, wherein the step of inoculating the skim milk with a coagulating enzyme comprises the step of inoculating the skim milk with calf rennet.

11. A method for manufacturing a skim milk product as defined in claim 1, wherein the step of inoculating the skim milk with a coagulating enzyme comprises the step of inoculating the skim milk with a microbial rennet.

12. A method for manufacturing a skim milk product as defined in claim 1, wherein the step of inoculating the skim milk with a coagulating enzyme comprises the step of inoculating the skim milk with a plant rennet.

13. A method for manufacturing a skim milk product as defined in claim 1, wherein the step of heat treating the inoculated skim milk product comprises the step of ultra-heat pasteurizing the inoculated skim milk to halt the reaction of the coagulating enzyme with the casein in the milk.

14. A method for manufacturing a skim milk product as defined in claim 1 wherein the incubation time period is adjusted in accordance with the chosen temperature so as to produce a desired quantity of aggregates of destabilized casein.

15. A method for manufacturing a lowfat milk product, the method comprising the steps of:
   (a) inoculating a lowfat milk with a coagulating enzyme to cleave a portion of casein in the lowfat milk so as to destabilize the casein;
   (b) incubating the inoculated lowfat milk for a period of time sufficient to allow the destabilized casein in the lowfat milk to form aggregates of destabilized casein so as to produce a lowfat milk product having a mouthfeel similar to milk having a higher milk-fat content; and
   (c) heat treating the inoculated lowfat milk to inactivate substantially all of the coagulating enzyme.

16. The method for manufacturing a lowfat milk product as defined in claim 15, further comprising the step of pre-heat treating the lowfat milk before the step of inoculating the lowfat milk with the coagulating enzyme.

17. A method for manufacturing a lowfat milk product as defined in claim 15, wherein the step of incubating the inoculated lowfat milk comprises the step of incubating the inoculated lowfat milk at a temperature in the range from about 35° F. to about 50° F.

18. A method for manufacturing a lowfat milk product as defined in claim 15, wherein the step of incubating the inoculated lowfat milk comprises the step of incubating the inoculated lowfat milk at a temperature in the range from about 35° F. to about 75° F.

19. A method for manufacturing a lowfat milk product as defined in claim 15, wherein the step of incubating the inoculated lowfat milk comprises the step of incubating the inoculated lowfat milk at a temperature in the range from about 35° F. to about 104° F.

20. A method for manufacturing a lowfat milk product as defined in claim 17, wherein the step of incubating the inoculated lowfat milk comprises the step of incubating the inoculated lowfat milk for a period in the range from about 30 minutes to about 60 minutes.

21. A method for manufacturing a lowfat milk product as defined in claim 18, wherein the step of incubating the inoculated lowfat milk comprises the step of incubating the lowfat milk for a period in the range from about 10 minute to about 90 minutes.

22. A method for manufacturing a lowfat milk product as defined in claim 19, wherein the step of incubating the inoculated lowfat milk comprises the step of incubating the lowfat milk for a period in the range from about 5 to about 90 minutes.

23. A method for manufacturing a lowfat milk product as defined in claim 15, wherein the method further comprises the step of storing the lowfat milk product until consumption so as to prevent spoiling of the lowfat milk product.

24. A method for manufacturing a lowfat milk product as defined in claim 23, wherein the step of storing the lowfat milk product comprises the step of storing the lowfat milk product in a refrigerated holding tank.

25. A method for manufacturing a lowfat milk product as defined in claim 15, wherein the step of inoculating the lowfat milk with a coagulating enzyme comprises the step of inoculating the lowfat milk with a calf rennet.

26. A method for manufacturing a lowfat milk product as defined in claim 15, wherein the step of inoculating the lowfat milk with a coagulating enzyme comprises the step of inoculating the lowfat milk with a microbial rennet.

27. A method for manufacturing a lowfat milk product as defined in claim 15, wherein the step of inoculating the lowfat milk with a coagulating enzyme comprises the step of inoculating the lowfat milk with a plant rennet.

28. A method for manufacturing a lowfat milk product as defined in claim 15, wherein the step of heat treating the inoculated lowfat milk comprises the step of ultra-heat pasteurizing the inoculated lowfat milk to halt the reaction of the coagulating enzyme with the casein in the lowfat milk.

29. A method for manufacturing a lowfat milk product as defined in claim 15 wherein the incubation time period is adjusted in accordance with the chosen temperature so as to produce a desired quantity of aggregates of destabilized casein.

30. A processed skim milk comprising:
skim milk treated with a coagulating enzyme so as to form aggregates of a portion of the casein in the skim milk, the processed skim milk having a resulting texture such that the mouthfeel of the processed skim milk is similar to the mouthfeel of milk having a higher milk-fat content, the processed skim milk being characterized by the absence of a casein aggregate gel network, and the coagulating enzyme being deactivated after aggregation of a portion of the casein in the skim milk wherein said deactivation occurs prior to the formation of a gel from the casein aggregates.

31. A processed skim milk product as defined in claim 30, wherein the coagulating enzyme comprises a proteolytic enzyme.

32. A processed skim milk product as defined in claim 30, wherein the coagulating enzyme comprises a rennet.

33. A processed skim milk product as defined in claim 32, wherein the coagulating enzyme comprises a calf rennet.

34. A processed skim milk product as defined in claim 32, wherein the coagulating enzyme comprises a microbial rennet.

35. A processed skim milk product as defined in claim 34, wherein the microbial rennet comprises *Mucor miehei*.

36. A processed skim milk product as defined in claim 34, wherein the microbial rennet comprises *Mucor pusillus*.

37. A processed skim milk product as defined in claim 34, wherein the microbial rennet comprises *Endothia parasitica*.

38. A processed skim milk product as defined in claim 34, wherein the microbial rennet comprises Bacillus spp.

39. A processed skim milk product as defined in claim 34, wherein the microbial rennet comprises Aspergillus spp.

40. A processed skim milk product as defined in claim 32, wherein the rennet comprises a plant rennet.

41. A processed skim milk product as defined in claim 30, wherein the coagulating enzyme is comprised of about 90 grams of rennet per 45 kilograms of skim milk.

42. A processed skim milk product as defined in claim 32, wherein the rennet is added to the skim milk at a temperature in the range from about 35° F. to about 104° F.

43. A processed skim milk product as defined in claim 42, wherein the rennet is allowed to react with the casein in the skim milk for a time period in the range from about 5 to about 90 minutes.

44. A processed skim milk product as defined in claim 30, wherein the coagulating enzyme acts on the k-casein in the milk.

45. A processed skim milk product as defined in claim 30, wherein the milk product maintains a mouthfeel similar to milk with a higher fat content during subsequent storage and use at temperatures ranging from normal refrigeration to normal cooking temperatures.

46. A processed skim milk product as defined in claim 30, wherein the casein aggregates in the milk product have a length in the range from about 0.5 to about 10 micrometers and a width in the range from about 0.5 to about 10 micrometers.

47. A processed skim milk product as defined in claim 30, wherein the processed milk product has a whiteness value in the range from about 55 to 65 L* units.

48. A processed skim milk product as defined in claim 30, wherein the processed milk product has a blueness value in the range from about −5 to about −2 b* units.

49. A processed lowfat milk product comprising:
lowfat milk treated with a coagulating enzyme so as to form aggregates of a portion of the casein in the milk, the processed lowfat milk product having a resulting texture such that the mouthfeel of the processed lowfat milk product is similar to the mouthfeel of milk having a higher milk-fat content, the processed lowfat milk product being characterized by the absence of a casein aggregate gel network, and the coagulating enzyme being deactivated after aggregation of a portion of the casein in the lowfat milk wherein said deactivation occurs prior to the fomation of a gel from the casein aggregates.

50. A processed lowfat milk product as defined in claim 49, wherein the coagulating enzyme comprises a rennet.

51. A processed lowfat milk product as defined in claim 50, wherein the coagulating enzyme comprises a calf rennet.

52. A processed lowfat milk product as defined in claim 50, wherein the coagulating enzyme comprises a microbial rennet.

53. A processed lowfat milk product as defined in claim 52, wherein the microbial rennet comprises *Mucor miehei*.

54. A processed lowfat milk product as defined in claim 52, wherein the microbial rennet comprises *Mucor pusillus*.

55. A processed lowfat milk product as defined in claim 52, wherein the microbial rennet comprises *Endothia parasitica*.

56. A processed lowfat milk product as defined in claim 52, wherein the microbial rennet comprises Bacillus spp.

57. A processed lowfat milk product as defined in claim 52, wherein the microbial rennet comprises Aspergillus spp.

58. A processed lowfat milk product as defined in claim 50, wherein the rennet comprises a plant rennet.

59. A processed lowfat milk product as defined in claim 49, wherein the coagulating enzyme is comprised of about 90 grams of rennet per 45 kilograms of lowfat milk.

60. A processed lowfat milk product as defined in claim 49, wherein the coagulating enzyme is added to the milk at a temperature in the range from about 35° F. to about 104° F.

61. A processed lowfat milk product as defined in claim 60, wherein the coagulating enzyme is allowed to react with the casein in the milk for a time period in the range from about 5 to about 90 minutes.

62. A processed lowfat milk product as defined in claim 49, wherein the coagulating enzyme acts on the k-casein in the milk.

63. A processed lowfat milk product as defined in claim 49, wherein the milk product maintains a mouthfeel similar to milk with a higher fat content during subsequent storage and use at temperatures ranging from normal refrigeration to normal cooking temperatures.

64. A processed lowfat milk product as defined in claim 49, wherein the casein aggregates in the milk product have a length in the range from about 0.5 to about 10 micrometers and a width in the range from about 0.5 to about 10 micrometers.

65. A processed lowfat milk product as defined in claim 49, wherein the processed milk product has a whiteness value in the range from about 70 to about 80 L* units.

66. A process lowfat milk product as defined in claim 49, wherein the processed milk product has a blueness value in the range from about −3.0 to about 0.0 b* units.

67. A skim milk product manufactured by the following process:
  (a) inoculating skim milk with a coagulating enzyme to cleave a portion of the casein in the skim milk so as to destablize the casin;
  (b) incubating the inoculated skim milk for a period of time sufficient to allow the destabilized casein in the skim milk to form aggregates of destabilized casein so as to produce a skim milk product having a mouthfeel similar to milk having a higher milk-fat content; and
  (c) heat treating the inoculated skim milk to inactivate substantially all of the coagulating enzyme.

68. A lowfat milk product manufactured by the following process:
  (a) inoculating lowfat milk with a coagulating enzyme to cleave a portion of the casein in the lowfat milk so as to destabilize the casein;
  (b) incubating the inoculated lowfat milk for a period of time sufficient to allow the destabilized casein in the milk to form aggregates of destabilized casein so as to produce a skim milk product having a mouthfeel similar to milk having a higher milk-fat content; and
  (c) heat treating the inoculated lowfat milk so as to inactivate substantially all of the coagulating enzyme.

69. A textured milk product comprising aggregates of casein micelles, said textured milk product providing a subjective sensation of creaminess similar to milk with a higher fat content.

70. A textured milk product as defined in claim 69 wherein the aggregates of casein micelles are contained in skim milk.

71. A textured milk product as defined in claim 69 wherein the aggregates of casein micelles are contained in lowfat milk.

72. A textured milk product as defined in claim 69 wherein the creamy sensation is maintained during subsequent storage and use at temperatures ranging from normal refrigeration to normal cooking temperatures.

73. A method for manufacturing a textured milk product, the method comprising the steps of:
  (a) inoculating milk with a coagulating enzyme to cleave a portion of the casein in the milk so as to destabilize the casein
  (b) incubating the inoculated milk for a period of time sufficient to allow the destabilized casein in the milk to form aggregates of destabilized casein so as to produce a desired texture; and
  (c) substantially halting the enzyme reaction.

74. The method for manufacturing a textured milk product as defined in claim 73 wherein the inoculated milk comprises skim milk.

75. The method for manufacturing a textured milk product as defined in claim 73 wherein the inoculated milk comprises lowfat milk.

76. The method for manufacturing a textured milk product as defined in claim 73 wherein the step of substantially halting the enzyme reaction comprises the addition of a large quantity of non-inoculated milk.

77. The method for manufacturing a textured milk product as defined in claim 73 wherein the step of substantially halting the enzyme reaction comprises heating.

78. The method for manufacturing a textured milk product as defined in claim 77 wherein the heating proceeds to a temperature in the range of from about 72° C. to about 142° C.

79. The method for manufacturing a textured milk product as defined in claim 78 wherein the temperature is maintained for a period of from about 6 seconds to about 16 seconds.

80. The method for manufacturing a textured milk product as defined in claim 77 wherein the heating proceeds to a temperature of about 63° C.

81. The method for manufacturing a textured milk product as defined in claim 80 wherein the temperature is maintained for a period of about 30 minutes.

* * * * *